United States Patent [19]

Naganuma et al.

[11] 4,078,055
[45] Mar. 7, 1978

[54] DEODORIZING AND SMELL-REMOVING COMPOSITION AND METHOD OF USING SAME

[75] Inventors: Yoshinori Naganuma, Hoya; Haruhiko Arai, Narashino, both of Japan

[73] Assignee: Kao Soap Co., Ltd., Tokyo, Japan

[21] Appl. No.: 670,735

[22] Filed: Mar. 26, 1976

[30] Foreign Application Priority Data

Apr. 11, 1975 Japan .................................. 50-44101

[51] Int. Cl.$^2$ ............................................ A61K 13/00
[52] U.S. Cl. ...................................... 424/76; 424/359
[58] Field of Search ................................ 424/359, 76

[56] References Cited

U.S. PATENT DOCUMENTS

| 3,316,175 | 4/1967 | Latos et al. ................ 424/168 X |
| 3,823,232 | 7/1974 | Galerne .................... 424/359 X |
| 3,829,563 | 8/1974 | Barry et al. ............... 424/168 X |
| 3,929,990 | 12/1975 | Green et al. ............... 424/168 X |

FOREIGN PATENT DOCUMENTS

| 21,519 | 10/1967 | Japan ........................................ 424/76 |
| 30,320 | 3/1971 | Japan ........................................ 424/76 |

OTHER PUBLICATIONS

De Navarre, International Encyclopedia of Cosmetic Material Trade Names, 1957, pp. 95 and 162.

*Primary Examiner*—Dale R. Ore
*Attorney, Agent, or Firm*—Blanchard, Flynn, Thiel, Boutell & Tanis

[57] ABSTRACT

Odoriferous materials and objects containing mercaptans, hydrogen sulfide and ammonia are deodorized with a deodorizing composition consisting essentially of a glycine type amphoteric surface active agent, and an adduct of ethylene oxide to castor oil, hydrogenated castor oil or lanolin and at least one specific phosphate.

10 Claims, No Drawings

DEODORIZING AND SMELL-REMOVING COMPOSITION AND METHOD OF USING SAME

BACKGROUND OF THE INVENTION

1. Field of Invention

The present invention relates to a deodorizing and smell-removing composition. More particularly, the invention relates to a composition which can remove bad smells effectively from dust bins, cattle stalls and the like by rapidly removing the smells of ammonia mercaptans and hydrogen sulfide, removal of which has been very difficult according to conventional techniques.

2. Description of Prior Art

It is known that deodorizing and smell-removing effects can be attained by glycine type amphoteric surface active agents. For example, there have heretofore been proposed a smell-removing agent comprising a glycine type amphoteric surface active agent and a non-ionic surface active agent (Japanese Patent Publication No. 16118/71), a deodorizing agent comprising a glycine type amphoteric surface active agent impregnated in a microporous molded article (Japanese Patent Publication No. 30320/71), and a deodorizing agent comprising a glycine type amphoteric surface active agent and an alkaline substance (Japanese Patent Laid-Open Application No. 17367/74).

However, satisfactory deodorizing and smell-removing effects cannot always be attained even according to these conventional techniques.

DESCRIPTION OF INVENTION

The inventors have made various research works on deodorizing and smell-removing methods using glycine type amphoteric surface active agents, and they have found that excellent deodorizing and smell-removing effects can be obtained when a glycine type amphoteric surface active agent is used in combination with a specific non-ionic surface active agent and a specific phosphoric acid ester salt. Based on this finding, the inventors have now completed the present invention.

The invention provides a process for deodorizing odoriferous materials and objects characterized by having one or more of mercaptans, hydrogen sulfide and ammonia as a bad-smelling component, which comprises applying to said material or object an effective deodorizing amount of a deodorizing composition essentially consisting of a glycine type amphoteric surface active agent represented by the following general formula (I):

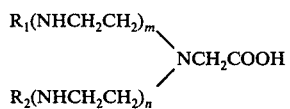

wherein $R_1$ stands for an alkyl group having 6 to 18 carbon atoms, $R_2$ stands for a hydrogen atom or an alkyl group having 6 to 18 carbon atoms, $m$ is an integer of 1 to 5, and $n$ is 0 or an integer of 1 to 5, an adduct or ethylene oxide to castor oil, hydrogenated castor oil or lanolin, and at least one phosphoric acid ester salt represented by any of the following general formulae (II), (III) and (IV):

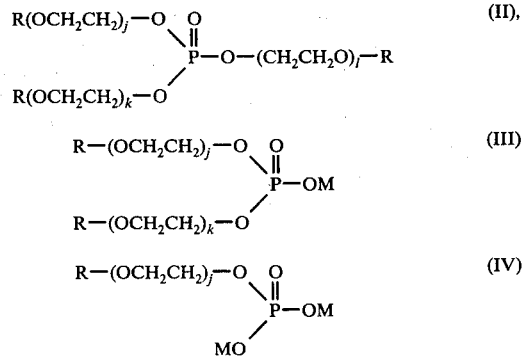

wherein R stands for an alkyl or alkenyl group having 8 to 22 carbon atoms, $j$, $k$ and $l$ each stand for 0 or an integer of 1 to 40, and M stands for a cation selected from alkali metals, ammonia and alkylolamines, the deodorizing composition being applied in an amount sufficient to substantially reduce the content of said bad-smelling component of the odoriferous material or object.

As the glycine type amphoteric surface active agent of above general formula (I) that is used in the present invention, there can be mentioned, for example, N-octylaminoethylglycine, N-aminoethyl-N-octylaminoethylglycine, N,N-di(octylaminoethyl)glycine, N,N-di[dodecyl-di(aminoethyl)]glycine, N,N-di[octyltetra(aminoethyl)]glycine, and organic and inorganic acid salts of these glycine compounds.

In the adduct of ethylene oxide to castor oil, hydrogenated castor oil or lanolin that is used in the present invention, it is preferred that the number of moles of ethylene oxide added be 1 to 300, especially 10 to 50.

As examples of the phosphoric acid ester salt of above general formula (II), (III) or (IV) that is used in the present invention, there can be mentioned alkali metal, ammonium or alkylol amine salts of mono-, di- or tri-dodecyl phosphates, alkali metal, ammonium or alkylol amine salts of mono-, di- or tri-(polyoxyethylenedodecyl-ether) phosphates, and alkali metal, ammonium or alkylol amine salts of polyoxyethyleneoctadecyl-ether sesquiphosphates. The alkali metal is preferred to be potassium or sodium.

When the deodorizing and smell-removing composition of the present invention is applied to actual uses, it is employed in the state of being dissolved or emulsified in water, an alkanol having one to 3 carbon atoms such as ethanol or a mixed solvent thereof as an inert carrier or diluent substance. If desired, another solvent, a stabilizer, a perfume and other additive may be incorporated into the composition of the present invention. In this case, the deodorizing and smell-removing agent comprises preferably 0.01 to 5% by weight of the glycine type amphoteric surface active agent preferably 0.2 to 1.0%; 0.01 to 5% by weight of the adduct of ethylene oxide to castor oil, hydrogenated castor oil or lanolin, preferably 0.2 to 1.0%; and 0.01 to 5% by weight of the phosphoric acid ester salt, preferably 0.2 to 1.0%.

By virtue of the feature of the deodorizing and smell-removing agent of the present invention that it comprises, as indispensable components, the glycine type amphoteric surface active agent, the adduct of ethylene oxide to castor oil, hydrogenated castor oil or lanolin and the phosphoric acid ester salt, the composition of the present invention can have very excellent deodorizing and smell-removing effects, and it can remove rapidly not only ammonia smell but also smells of mercaptans and hydrogen sulfide, removal of which has been difficult according to the conventional techniques. Accordingly, the composition of the present invention is very effective for removing bad smells from dust bins, cattle stalls and the like.

The present invention will now be described in detail by reference to the following Examples, in which all of "%" are by weight.

EXAMPLE 1

A deodorizing composition containing components indicated in Table 1 was prepared and the deodorizing effect was determined according to the following method.

A 500 ml-capacity wide-mouth bottle was charged with 20 g of thinly sliced fish meat (mackerel), and the fish meat was allowed to stand still at 30° C for 3 days to effect putrefaction. Then, 3 g of the sample of the deodorizing agent was sprayed to the putrefied fish meat, and the ammonia and mercaptan concentrations were measured at intervals by using a Kitagawa type vacuum gas detector to obtain results shown in Table 1.

Table 1

|  | Sample 1 | Sample 2 | Sample 3 | Sample 4 | Sample 5 | Sample 6 | Sample 7 |
|---|---|---|---|---|---|---|---|
| Composition (% by weight): |  |  |  |  |  |  |  |
| N,N-di(octylaminoethyl)glycine | 2 |  |  | 1.5 |  |  | 1 |
| Castor oil-ethylene oxide adduct (P = 25) |  | 2 |  | 0.5 |  |  | 0.5 |
| ammonium monododecyl phosphate |  |  | 2 |  |  |  | 0.5 |
| lauryl methacrylate |  |  |  |  | 2 |  |  |
| glyoxal |  |  |  |  |  | 2 |  |
| water | 98 | 98 | 98 | 98 | 98 | 98 | 98 |
| Measured value (ppm): |  |  |  |  |  |  |  |
| Ammonia: |  |  |  |  |  |  |  |
| before spraying | 40 | 38 | 35 | 40 | 42 | 41 | 43 |
| 1 hour after spraying | 15 | 41 | 30 | 15 | 40 | 15 | 7 |
| 3 hours after spraying | 10 | 35 | 30 | 10 | 35 | 10 | 2 |
| Ethylmercaptan: |  |  |  |  |  |  |  |
| before spraying | 150 | 145 | 150 | 150 | 155 | 148 | 140 |
| 1 hour after spraying | 85 | 140 | 140 | 80 | 150 | 80 | 55 |
| 3 hours after spraying | 80 | 130 | 145 | 80 | 150 | 70 | 40 |

As will be apparent from the results shown in Table 1, the deodorizing agent of the present invention (sample 7) has a much higher deodorizing effect to either ammonia or ethylmercaptan than deodorizing agents comprising one of the three indispensable components (samples 1 to 3), the deodorizing agent comprising both the glycine type surface active agent and the non-ionic surface active agent in combination (sample 4) and conventional deodorizing agents (samples 5 and 6).

EXAMPLE 2

A deodorizing composition containing components indicated in Table 2 was prepared, and its deodorizing effect was measured in the same manner as in Example 1. As the bad smell source, there was employed a mixture containing 3.75 g each of thinly sliced potato, onion, lettuce and cucumber and 7.5 g each of banana skin and apple, which had been allowed to stand still at 30° C for 3 days to effect putrefaction. Obtained results are shown in Table 2.

Table 2

|  | Sample 8 | Sample 9 | Sample 10 | Sample 11 | Sample 12 |
|---|---|---|---|---|---|
| Composition (% by weight): |  |  |  |  |  |
| N-laurylaminoethylglycine | 2 |  |  |  | 0.7 |
| lanoline-ethylene oxide adduct (P = 30) |  | 2 |  |  | 0.8 |
| potassium polyoxyethylene-dodecyl-ether sesquiphosphate (P = 9.3) |  |  | 2 |  | 0.5 |
| ethylene glycol monocrotonate |  |  |  | 2 |  |
| ethanol | 50 | 50 | 50 | 50 | 50 |
| water | 48 | 48 | 48 | 48 | 48 |
| Measured Value (ppm): |  |  |  |  |  |
| Ammonia: |  |  |  |  |  |
| before spraying | 15 | 15 | 16 | 15 | 17 |
| 1 hour after spraying | 8 | 12 | 17 | 10 | 5 |
| 3 hours after spraying | 7 | 12 | 16 | 8 | 2 |
| Ethylmercaptan: |  |  |  |  |  |
| before spraying | 20 | 18 | 17 | 20 | 18 |
| 1 hour after spraying | 8 | 15 | 15 | 12 | 4 |
| 3 hours after spraying | 8 | 15 | 15 | 8 | 2 |

As will be apparent from the results shown in Table 2, the deodorizing agent of the present invention (sample 12) has a better deodorizing effect than other samples.

EXAMPLE 3

| | |
|---|---|
| N-Aminoethyl-N-laurylaminoethylglycine | 0.5% |
| Hydrogenated castor oil-ethylene oxide adduct (P = 10) | 0.2% |
| Sodium dioctyl phosphate | 0.3% |
| Ethanol | 30% |
| Propylene glycol | 5% |
| Perfume | 1% |
| Water | 63% |

A deodorizing and smell-removing composition having the above recipe was prepared, and the composition was filled into an aerosol can together with a propellant. When the composition was sprayed to raw kitchen refuse, a high deodorizing effect was obtained.

EXAMPLE 4

| | |
|---|---|
| N,N-Di[dodecyl-tri(aminoethyl)]glycine | 0.75% |

| | |
|---|---|
| Castor oil-ethylene oxide adduct ($\overline{P}$ = 50) | 0.20% |
| Tridecyl phosphate | 0.05% |
| Diethylene glycol | 5.0% |
| Ethanol | 40.0% |
| Perfume | 0.3% |
| Water | 53.7% |

A deodorizing and smell-removing composition having the above recipe was prepared. Also this composition had a high deodorizing effect to raw kitchen refuse.

The embodiments of the invention in which an exclusive property or privilege is claimed are defined as follows:

1. A composition for deodorizing odoriferous materials and objects characterized by having one or more of mercaptans, hydrogen sulfide and ammonia as a bad-smelling component, which consists essentially of a mixture of from 0.01 to 5 weight percent of a glycine type amphoteric surface active agent having the formula (I):

wherein $R_1$ is alkyl having 6 to 18 carbon atoms, $R_2$ is hydrogen or alkyl having 6 to 18 carbon atoms, $m$ is an integer of 1 to 5, and $n$ is zero or an integer of 1 to 5, or organic or inorganic acid salts of said surface active agent, from 0.01 to 5 weight percent of an adduct of from 1 to 300 moles of ethylene oxide to castor oil, an adduct of from 1 to 300 moles of ethylene oxide to hydrogenated castor oil or an adduct of from 1 to 300 moles of ethylene oxide to lanolin; from 0.01 to 5 weight percent of at least one phosphoric acid ester salt selected from the group consisting of salts having the formulae (II), (III) and (IV):

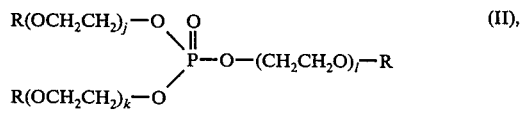

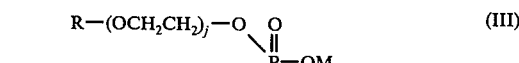

and

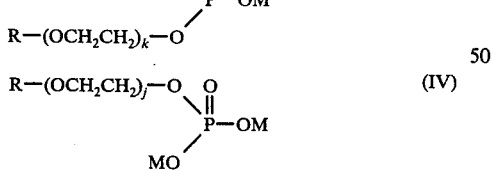

wherein R is alkyl or alkenyl having 8 to 22 carbon atoms, $j$, $k$ and $l$ each are zero or an integer of 1 to 40, and M is a cation selected from the group consisting of alkali metal, ammonia and alkylolamine, and the balance of the composition consists essentially of an inert carrier or diluent substance.

2. A composition according to claim 1, in which said carrier or diluent substance is selected from the group consisting of water, alkanol having one to three carbon atoms and mixtures thereof.

3. A composition according to claim 2 containing from 0.2 to 1.0 weight percent of said surface active agent, from 0.2 to 1.0 weight percent of said adduct and from 0.2 to 1.0 weight percent of said phosphoric acid ester salt.

4. A composition according to claim 3, in which said glycine type amphoteric surface active agent is selected from the group consisting of N-octylaminoethylglycine, N-aminoethyl-N-octylaminoethylglycine, N,N-di(octylaminoethyl)glycine, N,N-di(dodecyl-di(aminoethyl)glycine, N,N-di(octyl-tetra(aminoethyl) )glycine, and organic and inorganic acid salts thereof.

5. A composition according to claim 3, in which said phosphoric acid ester salt is selected from the group consisting of alkali metal salt of mono-dodecylphosphate, alkali metal salt of di-dodecylphosphate, alkali metal salt of tri-dodecylphosphate, ammonium salt of mono-dodecylphosphate, ammonium salt of didodecylphosphate, ammonium salt of tri-dodecylphosphate, alkylolamine salt of mono-dodecylphosphate, alkylolamine salt of di-dodecylphosphate, alkylolamine salt of tri-dodecylphosphate, alkali metal salt of mono-(polyoxy-ethylene-dodecyl-ether) phosphate, alkali metal salt of di-(polyoxy-ethylene-dodecylphosphate alkali metal salt of tri-(polyoxy-ethylenedodecyl-ether) phosphate, ammonium salt of mono(polyxoyethylene-dodecyl-ether) phosphate, ammonium salt of di-(polyoxyethylene-dodecyl-ether) phosphate, ammonium salt of tri-(polyoxyethylene-dodecyl-ether) phosphate, alkylolamine salt of mono-(polyoxyethylenedodecyl-ether) phosphate, alkylolamine salt of di(polyoxyethylene-dodecyl-ether) phosphate, alkylolamine salt of tri-(polyoxy-ethylene-dodecyl-ether) phosphate, alkali metal salt of polyoxyethylene-octa-decyl-ether sesquiphosphate, ammonium salt of polyoxyethyleneoctadecyl-ether sesquiphosphate, and alkylolamine salt of polyoxyethylene-octadecyl-ether sesquiphosphate.

6. A method for deodorizing odoriferous materials and objects characterized by having one or more of mercaptans, hydrogen sulfide and ammonia as a bad-smelling component, which comprises applying to said material or object an effective deodorizing amount of a deodorizing composition consisting essentially of a glycine type amphoteric surface active agent having the formula (I):

wherein $R_1$ is alkyl having 6 to 18 carbon atoms, $R_2$ is hydrogen or alkyl having 6 to 18 carbon atoms, $m$ is an integer of 1 to 5, and $n$ is zero or an integer of 1 to 5, or organic or inorganic acid salts of said surface active agent, an adduct of from 1 to 300 moles of ethylene oxide to castor oil, an adduct of from 1 to 300 moles of ethylene oxide to hydrogenated castor oil or an adduct of from 1 to 300 moles of ethylene oxide to lanolin, and at least one phosphoric acid ester salt selected from the group consisting of salts having the formulae (II), (III) and (IV):

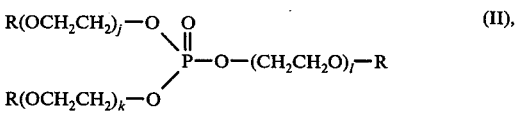

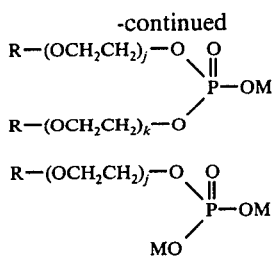

wherein R is alkyl or alkenyl having 8 to 22 carbon atoms, $j$, $k$ and $l$ each are zero or an integer of 1 to 40, and M is a cation selected from the group consisting of alkali metal, ammonia and alkylolamines, the deodorizing composition being applied in an amount sufficient to substantially reduce the content of said bad-smelling component of the odoriferous material or object.

7. The method according to claim 6, wherein said applying is accomplished by dissolving or emulsifying said deodorizing composition in water, an alkanol having one to three carbon atoms or mixtures thereof, and applying the dissolved or emulsified deodorizing composition to the odoriferous material or object.

8. The method according to claim 7, wherein the solution or emulsion contains from 0.01 to 5 weight percent of said glycine type amphoteric surface active agent, from 0.01 to 5 weight percent of said adduct and from 0.01 to 5 weight percent of said phosphoric acid ester salt.

9. The method according to claim 9, in which said glycine type amphoteric surface active agent is selected from the group consisting of N-octylaminoethylglycine, N-aminoethyl-N-octylaminoethylglycine, N,N-di(octylaminoethyl)glycine, N,N-diglycine, and organic and inorganic acid salts thereof.

10. The method according to claim 8, in which said phosphoric acid ester salt is selected from the group consisting of alkali metal salt of mono-dodecylphosphate, alkali metal salt of di-dodecylphosphate, alkali metal salt of tri-dodecylphosphate, ammonium salt of mono-dodecylphosphate, ammonium salt of didodecylphosphate, ammonium salt of tri-dodecylphosphate, alkylolamine salt of mono-dodecylphosphate, alkylolamine salt of di-dodecylphosphate, alkylolamine salt of tri-dodecylphosphate, alkali metal salt of mono-(polyoxy-ethylene-dodecyl-ether) phosphate, alkali metal salt of di-(polyoxy-ethylene-dodecylphosphate), alkali metal salt of tri-(polyoxy-ethylenedodecyl-ether) phosphate, ammonium salt of mono(polyoxyethylene-dodecyl-ether) phosphate, ammonium salt of di-(polyoxyethylene-dodecyl-ether) phosphate, ammonium salt of tri-(polyoxyethylene-dodecyl-ether) phosphate, alkylolamine salt of mono-(polyoxyethylenedodecyl-ether) phosphate, alkylolamine salt of di-(polyoxyethylene-dodecyl-ether) phosphate, alkylolamine salt of tri-(polyoxy-ethylene-dodecyl-ether) phosphate, alkali metal salt of polyoxyethylene-octadecyl-ether sesquiphosphate, ammonium salt of polyoxyethyleneoctadecyl-ether sesquiphosphate, and alkylolamine salt of polyoxyethylene-octadecyl-ether sesquiphosphate.

* * * * *

UNITED STATES PATENT OFFICE
CERTIFICATE OF CORRECTION

Patent No. 4 078 055    Dated  March 7, 1978

Inventor(s)  Yoshinori Naganuma et al

It is certified that error appears in the above-identified patent and that said Letters Patent are hereby corrected as shown below:

Column 6, line 21;  change "dodecylphosphate alkali" to ---dodecyl-ether) phosphate, alkali---.

Column 6, line 23;  change "polyxoyethylene" to ---polyoxyethylene---.

Column 6, line 31;  change "polyxoyethylene" to ---polyoxyethylene---.

Column 7, line 32;  change "9" to ---8---.

Column 8, line 3;  delete "N,N-diglycine" and replace by ---N,N-di-[dodecyl-di(aminoethyl)]glycine, N,N-di[octyl-tetra(aminoethyl)]glycine---.

Signed and Sealed this

Fifth Day of September 1978

[SEAL]

Attest:

RUTH C. MASON
Attesting Officer

DONALD W. BANNER
Commissioner of Patents and Trademarks

UNITED STATES PATENT OFFICE
CERTIFICATE OF CORRECTION

Patent No. 4,078,055    Dated March 7, 1978

Inventor(s) Yoshinori Naganuma et al

It is certified that error appears in the above-identified patent and that said Letters Patent are hereby corrected as shown below:

Column 8, line 16;  change "dodecylphosphate)," to

---dodecyl-ether) phosphate,---.

Column 8, line 18;  change "polyxoyethylene" to

---polyoxyethylene---.

Signed and Sealed this

Fifth Day of September 1978

[SEAL]

Attest:

RUTH C. MASON
Attesting Officer

DONALD W. BANNER
Commissioner of Patents and Trademarks